United States Patent [19]

Lloyd

[11] 4,149,869

[45] Apr. 17, 1979

[54] SEED COATING TECHNIQUES

[75] Inventor: John M. Lloyd, Nelson, New Zealand

[73] Assignee: Coated Seed Limited, Christchurch, New Zealand

[21] Appl. No.: 829,096

[22] Filed: Aug. 30, 1977

[30] Foreign Application Priority Data

Sep. 7, 1976 [NZ] New Zealand .................... 181956

[51] Int. Cl.$^2$ .................... A01N 21/02; C05G 3/08
[52] U.S. Cl. .................................... 71/7; 71/15; 47/57.6; 106/138; 195/50; 428/22
[58] Field of Search ............... 47/57.6; 71/7, 10, 15, 71/22, 64 G; 427/4; 106/138, 146, 148; 195/76, 79, 59, 50; 428/22, 15

[56] References Cited

U.S. PATENT DOCUMENTS

| | | | |
|---|---|---|---|
| 2,553,577 | 5/1951 | Hale et al. | 47/57.6 |
| 2,726,948 | 12/1955 | Erickson | 71/7 |
| 2,995,867 | 8/1961 | Burton | 71/7 |
| 3,460,492 | 8/1969 | Dickinson et al. | 47/57.6 |
| 3,499,748 | 3/1970 | Fraser | 71/7 |
| 3,616,236 | 10/1971 | Delin | 195/79 |
| 3,698,133 | 10/1972 | Schreiber | 47/57.6 |

FOREIGN PATENT DOCUMENTS

7272337 9/1973 Japan ....................... 47/57.6

OTHER PUBLICATIONS

Hackh's Chemical Dictionary; 1969; 4th Ed., McGraw-Hill Book Comp., N.Y., p. 137.
Principles of Dairy Chemistry, 1959, Chapman & Hall Ltd., p. 115, Jenness et al.

*Primary Examiner*—Kenneth M. Schor
*Attorney, Agent, or Firm*—Wenderoth, Lind & Ponack

[57] ABSTRACT

Seeds, for example, legume seeds, are coated with a mixture containing a caseinate salt and viable rhizobia bacteria.

16 Claims, No Drawings

SEED COATING TECHNIQUES

This invention relates to seed coating techniques, more particularly but not exclusively for coating legume seeds.

Coating seed in order to improve germination characteristics and to provide other materials for assisting the plant to become established has been practised for a number of years. Thus, coating of seeds with nutrient materials, fungicides, herbicidal agents, systemic insecticides are now common practice. With legume seeds, it is now highly recommended to inoculate the seeds with the required rhizobia bacteria in order to improve nodulation of the legume plants.

While many seed coating techniques as practised in the art have proven successful in improving germinating characteristics of plants, such as legume plants, there is a continuing search for improvement in order to provide even better results.

One particular difficulty that has emerged from research on legume seeds is that the viable bacteria are susceptible to toxic exudates from legume seeds. This can lead to a significant reduction in effective bacteria counts on the seeds and can well lead to situations where a low degree of effective nodulation of such coated seeds on planting is achieved.

We have now found that by incorporating a caseinate salt in the coating, survival of rhizobia bacteria can be noticeably increased. Without being bound by any particular theory it is considered that the caseinate salt inter alia improves the survival of the bacteria by reducing the toxic effect of the toxic exudates from the legume seed.

Thus, in a first form of this invention there is provided a coated legume seed in which the coating comprises a caseinate salt, together with viable rhizobia bacteria of the desired species.

We have further found that a caseinate salt is a nutrient source for rhizobia and, therefore, besides the increase in viability of the bacteria by the apparent inhibiting action of the caseinate salt on the effect of the toxic exudates, the caseinate salt further assists the growth of the organisms.

Much research in the field of coated seeds has been directed towards the particular adhesives that can be used to bind the desired materials to the seed itself. Generally a good adhesive needs to be effective on application at low concentrations of the order of 10 to 20% to hold the coating intact. With commercial coated seeds, the seeds need to be dried in order that the coating then becomes firmly attached to the seed for storage and shipment and the dried adhesive needs to form a flexible film so that the coating remains on the seed during handling. Finally, the adhesive needs to be such that it will redissolve or redisperse on planting, enabling dispersion of the materials in the seed coating to perform their desired function. In certain circumstances other specific properties may be required in a seed coating and there have been suggestions of using water insoluble adhesives to delay the release of particular reagents in the coating or partially soluble adhesives in order to delay the release of the particular materials and to delay germination of the plant but these particular types of adhesives are not generally required under normal conditions in New Zealand.

Research for an adhesive having these three main criteria for effectiveness, together with low cost, has not proven to be totally successful.

It has now been found that a caseinate salt does satisfy the major criteria for a good adhesive, namely being suitable for use in low concentration solutions, drying to a flexible film and having good adhesive characteristics for binding the coating materials to the seed and finally being water soluble in order to permit dispersion of the coating materials.

Thus, in a further form of the invention there is provided a coated seed especially a coated legume seed wherein the coating contains as an adhesive a caseinate salt.

Caseinate salts are known materials in the art which can be prepared from casein, a slightly acidic, virtually insoluble powder material, by neutralization thereof with an alkaline solution forming a water soluble salt with the alkaline agent. Salts which can be employed in this invention are preferably the alkali metal salts such as sodium or potassium but other salts such as alkaline earth metals, e.g. calcium or ammonium salts of ammonia or organic amines can also be used.

When using the caseinate salt in coating legume seeds, it is desirable to ensure that the solution or suspension has a pH close to neutral. For this reason it is desirable to prepare the caseinate salt specifically for the seed coating techniques of this invention and such can be done by dispersing the casein powder in water generally assisted by stirring, to which is then added the alkaline material to form the caseinate salt. The pH of the solution is monitored in order that the final solution has a pH in the range between 6.5 and 7. Provided sufficient concentration of the caseinate salt is present, the solution can be used as such as the adhesive in the coating of the seeds, or for the other purposes of this invention.

The alkaline agents to react with the casein to form the caseinate salt can be an alkali metal hydroxide or carbonate or an hydroxide or carbonate of other suitable salt forming agents.

Both sodium and potassium caseinate have proved to be substantially equally effective as adhesives in coating legume seeds and for maintaining good survival rates of rhizobia bacteria in such coatings. Potassium is preferred as it may assist in the growth of the rhizobia bacteria by providing a potassium nutrient source.

Other materials required or desired in the coating on the seed can be incorporated in the adhesive solution, for example a mixture of peat and dolomite which is known to be of value in assisting the maintenance of the viability of the bacteria, and the rhizobia inoculant itself, generally as a water slurry.

Generally the caseinate salt as an adhesive will be employed as a solution in water in a concentration based on dry weight of from 10 to 20%. Higher concentrations can be used but the adhesive effect achieved is not materially increased and moreover the solutions become viscous, making it difficult to process, for example when adding further materials to such adhesive solution. A satisfactory adhesive formulation is 15% by weight of a caseinate salt such as potassium caseinate in solution in a slurry of water plus inoculant. The seed can then be coated with this adhesive mixture and any additional ingredients such as lime as are required in the art can be applied at the same weight per seed as is practised in the art. Seeds when coated can then be dried in order to provide a firm coating which has also been found to assist in increasing the survival rate of rhizobia bacteria in the coating. The drying is carried out at a temperature which will not materially affect the viability of the bacteria, again in a manner which is well known in the art. Suitable drying conditions are at temperatures in the range of 10° C. to 25° C. preferably assisted by a reduction of pressure to less than 10 mm Hg (TORR).

The following examples illustrate the invention:

EXAMPLE 1

A 100 kilo batch of 15% caseinate adhesive is prepared as follows:

1. Add 14.5 kg casein powder to 75 kg water (20°–30° C.) and stir for approximately 10 mins. to allow casein to disperse and hydrate.
2. Dissolve 0.525 kg commercial grade potassium hydroxide in 4.475 kg of cold water and add to the casein suspension above. Stir for 15–20 mins. pH is adjusted by either addition of casein or potassium hydroxide to be from 6.5–7.0.
3. Add 5.5 kg inoculant/water slurry.

This adhesive cannot be held for lengthy periods after manufacture, because of its ability to support the growth of a wide range of microorganisms besides the desired rhizobia.

EXAMPLE 2

This example illustrates the method of preparing coated seeds in accordance with this invention.

Formula 100 kilos white clover seed
18.5 kilos caseinate adhesive (about 15% solids).
1.5 kilos slurry comprising peat inoculant dispersed in water.
75 kilos fine lime (ground to a fineness whereby a minimum of 98% by weight passes a 300 mesh British Standard test sieve, i.e. 53 microns).

Method

1. Place white clover seed in a large concrete mixer with vanes removed or other open mouthed rotating bowl.
2. Thoroughly mix the inoculum slurry with caseinate adhesive and apply to seed which is rotating within the bowl. A manually operated wooden paddle or other device is used to facilitate blending of the adhesive and coating material with the seed.
3. When adhesive/inoculum mixture is evenly distributed throughout the seed mass, add the lime and continue rolling until seeds have separated and the lime has adhered. The quantity of adhesive and lime may be adjusted to compensate for differences in absorbent capacity and surface area between different lines of white clover seed.
4. The coated seeds are then dried at a temperature preferably not exceeding 25° C. under a pressure of preferably less than 10 mm Hg.

The following trials give comparison tests of survival of rhizobia bacteria on seeds coated using a standard commercial adhesive and the potassium caseinate adhesive of this invention:

Trial 1

Lucerne samples checked immediately and after the stated periods of storage at room temperature. (Results expressed as number of rhizobia per gram of seed).

|  | Immediate | 11 days | 37 days |
|---|---|---|---|
| Standard adhesive | 45000 | 11,250 | 1475 |
| Potassium Caseinate adhesive | 45000 | 25,750 | 3400 |

Trial 2

Lucerne and white clover samples checked immediately and after the stated periods of storage at room temperature. (Results expressed as number of rhizobia per gram of seed).

|  | Immediate | 7 days | 14 days | 28 days |
|---|---|---|---|---|
| White clover "Standard" | 1,030,000 | 56,000 | 4,500 | — |
| White clover "caseinate" | 1,400,000 | 110,000 | 5,800 | — |
| Lucerne "Standard" | 1,800,000 | 1,000,000 | — | 13,000 |
| Lucern "caseinate" | 1,800,000 | 1,250,000 | — | 32,000 |

EXAMPLE 3

The survival of *Rhizobium trifolii* on white clover seed coated with lime using a potassium caseinate adhesive was compared to similar coated seeds using a gum arabic adhesive.

The materials employed were as follows:

white clover seed (*Trifolium repens*);
a 15% w/w aqueous solution of gum arabic as the adhesive for half of the seeds (Sample A);
a 15% w/w aqueous solution of potassium caseinate as the adhesive on the other half (Sample B);
Rhizocote (an inoculant sold commercially by Coated Seed Limited, containing a suitable strain of *Rhizobium trifolii;*
finely ground limestone (that sold under the brand name "green square" by Mintech (N.Z.) Limited, Nelson, New Zealand, which is essentially a 98% pure limestone of a particle size such that a minimum of 98% by weight passes a 300 mesh British Standard sieve (i.e. 53 microns).

The seeds were coated as described in example 2 in the following proportions:

1000 grams white clover seed;
60 grams adhesive;
6.4 grams of the inoculant dispersed in the adhesive, and;
500 grams of fine lime.

In view of the difficulty in achieving a stable coating with gum arabic after drying, and thus in order that the comparison between the survival rates of rhizobia in the two samples was as analogous as possible, bacteria counts were conducted without drying. The quantity of adhesive was considered to be sufficient to hold the coating intact.

The coated white clover seeds of samples A and B were prepared within a 15 minute period and stored in the undried state in an air tight container at 25° C. Representative 50 gram samples were removed at intervals and viable rhizobia numbers ascertained by plant infection techniques using table 3.5A from "A manual for the practical study of Root Nodule Bacteria" by J. M. Vincent. The results are as follows:

TABLE 3

| (Most probable number of *Rhizobium trifolii* per seed): | | |
|---|---|---|
| Days after coating | Sample A | Sample B |
| 1 | 2,525 | 4,545 |
| 7 | 434 | 2,525 |

EXAMPLE 4

Independent field trials were carried out by oversowing coated seeds in field plots approximately 20 days after manufacture of the coated seeds, at a rate of 8.75 kg/ha. The trial site was at an altitude of 600 meters with a soil type being high country, yellow brown earth having a pH of 4.7 with existing vegetation being snow tussock, browntop and sweet vernal grasses.

A basal dressing of molybdic superphosphate was applied at the rate of 400 kg/ha prior to sowing. Each sample was oversown onto 4 replicate trial plots and 20 healthy seedlings were identified in each plot by pegging at the cotyledon stage. The number of healthy seedlings at each pegged site was recorded three months later.

Sample C of the coated seeds employed a standard adhesive while sample A was prepared by the method described under Example 2.

The results are shown in the following table:

TABLE 4

| Sample employed | Rhizobia per seed at time of sowing | Percentage healthy seedlings established (the mean of 4 plots) |
|---|---|---|
| C | 920 | 43 |
| A | 420 | 61 |

This table demonstrates that despite fewer rhizobia at the time of sowing the sample prepared with the caseinate adhesive gave a 41.8% increase in seedling establishment.

It is considered that the higher rate of establishment from the sample using the caseinate adhesive was due mainly to improved nodulation which is attributed to better survival of rhizobia on Sample A after planting the seeds.

In this example no count was taken of the rhizobia per seed at the time of manufacture. Hence the lower count of rhizobia at the time of the trial in Sample A as compared to the Sample C, does not indicate in any way that the rhizobia on Sample A did not survive in storage conditions as well as those in Sample C. As demonstrated in Trials 1 and 2 under identical test conditions, seeds coated with caseinate adhesive gave a better survival ratio of rhizobia in comparison to those using the standard adhesive.

I claim:

1. A coated legume seed in which the coating comprises an adhesive and viable rhizobia bacteria, wherein the adhesive contains a man-made caseinate salt formed by reaction of casein with a salt forming alkaline agent in solution.

2. A coated legume seed as claimed in claim 1 in which the caseinate salt is a salt with an alkali metal, an alkaline earth metal, ammonia or an organic amine.

3. A coated legume seed as claimed in claim 1 wherein the salt is a salt with an alkali metal.

4. A coated legume seed as claimed in claim 3 wherein the alkali metal is potassium.

5. A coated legume seed as claimed in claim 1 wherein the caseinate salt is formed by reaction of casein with a salt forming alkaline agent in solution, and this solution is employed in the coating on the seed.

6. A coated legume seed in which the coating contains viable rhizobia bacteria and, as an adhesive, a material containing a man-made caseinate salt formed by reaction of casein with a salt forming alkaline agent in solution.

7. A coated seed as claimed in claim 6 wherein the caseinate salt is formed from an alkali metal, an alkaline earth metal, ammonia, or an organic amine.

8. A coated seed as claimed in claim 7 wherein the salt is formed from an alkali metal.

9. A coated seed as claimed in claim 8 wherein the alkali metal is potassium.

10. A coated seed as claimed in claim 6 wherein the caseinate salt is prepared as a solution having a caseinate salt concentration of from 10 to 20 percent by weight of the solution.

11. A coated seed as claimed in claim 10 wherein the caseinate salt solution is prepared by reacting casein with a salt forming agent in solution and adjusting the pH of the solution to between 6.5 and 7, and the solution is employed as the adhesive.

12. A coated seed as claimed in claim 5 wherein, after coating the seeds with the solution, the coated seeds are dried.

13. A coated seed as claimed in claim 11 wherein additional materials desired in the coating are incorporated in the caseinate salt solution.

14. A coated seed as claimed in claim 13 wherein a rhizobia inoculant is added to the caseinate salt solution.

15. A coated seed as claimed in claim 11 wherein, after coating the seeds with the solution, the coated seeds are dried.

16. A coated legume seed comprising a coating of rhizobia bacteria and lime bonded to the seed with an alkali metal caseinate.

* * * * *